United States Patent
Bahner

(10) Patent No.: US 9,821,077 B2
(45) Date of Patent: Nov. 21, 2017

(54) DIAGNOSTIC SUBSTANCES FOR OPTICAL IMAGING TESTING ON THE BASIS OF NANOPARTICULAR FORMULATIONS

(75) Inventor: Malte Bahner, Berlin (DE)

(73) Assignee: NANOPET PHARMA GMBH, Berlin (DE)

(*) Notice: Subject to any disclaimer, the term of this patent is extended or adjusted under 35 U.S.C. 154(b) by 0 days.

(21) Appl. No.: 12/677,871

(22) PCT Filed: Sep. 12, 2008

(86) PCT No.: PCT/EP2008/062193
§ 371 (c)(1),
(2), (4) Date: Mar. 12, 2010

(87) PCT Pub. No.: WO2009/034177
PCT Pub. Date: Mar. 19, 2009

(65) Prior Publication Data
US 2010/0303732 A1    Dec. 2, 2010

(30) Foreign Application Priority Data
Sep. 14, 2007   (EP) .................................. 07116409

(51) Int. Cl.
A61K 49/18    (2006.01)
A61K 49/00    (2006.01)

(52) U.S. Cl.
CPC ...... *A61K 49/0034* (2013.01); *A61K 49/0032* (2013.01); *A61K 49/0082* (2013.01)

(58) Field of Classification Search
CPC ............ A61K 49/0032; A61K 49/0082; A61K 49/0034
See application file for complete search history.

(56) References Cited

U.S. PATENT DOCUMENTS

| | | | |
|---|---|---|---|
| 6,123,923 A * | 9/2000 | Unger | A61K 49/0002 424/450 |
| 6,424,857 B1 | 7/2002 | Henrichs et al. | |
| 7,682,603 B2 | 3/2010 | Hammer et al. | |
| 7,803,397 B2 | 9/2010 | Heyes et al. | |
| 8,709,483 B2 * | 4/2014 | Farokhzad et al. | 424/489 |
| 2003/0152635 A1 | 8/2003 | Heurtault et al. | |
| 2005/0019265 A1 | 1/2005 | Hammer et al. | |
| 2005/0175682 A1 | 8/2005 | Heyes et al. | |
| 2005/0180922 A1 | 8/2005 | Discher et al. | |
| 2005/0214378 A1 | 9/2005 | Hoarau et al. | |
| 2006/0140865 A1 | 6/2006 | Chang et al. | |
| 2008/0019908 A1 * | 1/2008 | Akitsu et al. | 424/9.1 |
| 2010/0144899 A1 | 6/2010 | Goutayer et al. | |
| 2010/0284932 A1 | 11/2010 | Goutayer et al. | |
| 2011/0091525 A1 | 4/2011 | Heyes et al. | |

FOREIGN PATENT DOCUMENTS

| | | |
|---|---|---|
| JP | 2005022045 | 1/2005 |
| JP | 2007500192 A | 1/2007 |
| JP | 2007505954 A | 3/2007 |
| WO | 9852609 A1 | 11/1998 |
| WO | 03084869 A2 | 10/2003 |
| WO | 2005014051 A1 | 2/2005 |
| WO | 2005016259 A2 | 2/2005 |
| WO | 2005026372 A1 | 3/2005 |
| WO | 2006117301 A1 | 11/2006 |
| WO | 2008102065 A1 | 8/2008 |
| WO | 2008125747 A2 | 10/2008 |

OTHER PUBLICATIONS

Arun et al., J. Phys. Chem. A, vol. 109, No. 25, 2005.*
Coon et al., Cancer Research 51, 897-902, (Feb. 1, 1991).*
Bocca, et al. "Phagocytic uptake of fluorescent stealth and non-stealth solid lipid nanoparticles." (International Journal of Pharmaceutics), Dec. 15, 1998, 185-193, 175:2.
Sinha, et al. "Biodegradable PEGylated Microspheres and Nanospheres." (American Journal of Drug Delivery), 2004, 157-171, 2:3.
Office Action from corresponding Chinese Patent Application No. 200880106601.3 dated Mar. 8, 2013.
"Ester Bond" The School of Biomedical Sciences Wiki, https://teaching.ncl.ac.uk/bms/wiki/index.php/Ester_bond, [Nov. 12, 2012], 1 page.
"Opaque Liquid Detergent", Professional Committee of Science & Technology under China Cleaning Industry Association and China Informational Center of Daily Chemical Industry, Formulation Technology of Conventional Detergents, p. 39, [Published on May 31, 2003].
Yupu Fu, "Disperse System and Classification Thereof", Multi-Media, Physical Chemistry, vol. 2, p. 302, [Published on Dec. 31, 1998].
Official Action related to corresponding Chinese Patent Application No. 200880106601.3 dated Sep. 30, 2013.
Official Action related to corresponding Canadian Patent Application No. 2,699,341 dated Mar. 5, 2014.

* cited by examiner

Primary Examiner — Robert Cabral
(74) Attorney, Agent, or Firm — Millen White Zelano and Branigan, PC; Csaba Henter; John Sopp

(57) ABSTRACT

The present invention relates to the provision of nanoparticular formulations comprising a PEG-alkyl block copolymer and a near infrared fluorescent dye, the preparation of these nanoparticular formulations, pharmaceutical compositions comprising the nanoparticular formulations of the present invention, as well as their use as contrast medium.

21 Claims, 13 Drawing Sheets

Figu. 4C:

DIAGNOSTIC SUBSTANCES FOR OPTICAL IMAGING TESTING ON THE BASIS OF NANOPARTICULAR FORMULATIONS

The present invention relates to the provision of nanoparticular formulations comprising a PEG-alkyl block copolymer and a near infrared (NIR) fluorescent dye, the preparation of these nanoparticular formulations, pharmaceutical compositions comprising the nanoparticular formulations of the present invention, as well as their use as contrast medium.

Nowadays, the use of imaging processes plays a decisive role in the diagnosis, therapy and prophylaxis of diseases. More than 300 million imaging tests are carried out in clinical medicine each year. Processes such as ultrasound technology or X-ray-based testing, which are easy to carry out from a technical point of view, account for the majority of these tests. Another process which is easy to carry out from a technical point of view is optical imaging.

Optical imaging is a well-established diagnostic imaging process. While white light is used to screen organs (diaphanoscopy) in the simplest variation of this process, technically more sophisticated processes use light with clearly defined spectral properties. This way, unspecific background signals can be reduced while at the same time the depth of penetration of the diagnostic light is increased. Both parameters significantly influence the diagnostic accuracy of optical imaging.

Another possibility of improving the specificity and sensitivity of optical imaging is the use of fluorescent dyes. Various diagnostic fluorescent dyes have been available for about three to four decades. The class of substances of polymethine dyes, in particular cyanine dyes, is particularly important in this respect. Indocyanine green (ICG) is a known fluorescent dye which is widely used in optical imaging. The main field of application of ICG is fluorescence angiography in ophthalmology and in vascular surgery. The use of ICG allows the representation of the vessels. This way, the physician is for example able to detect the new formation of pathological vessels which indicate a disease. Another very important application is vascular surgery. By means of a fluorescent dye, it can be verified whether certain plastic surgeries at a vessel had the desired results. For instance, if an intravenously injected contrast medium escapes at a certain location of the vessel, it clearly indicates to the surgeon that the operation was not successful. ICG is suitable for these applications since it does not leave the vascular bed to concentrate in the extravascular space since it is completely bound to plasma proteins.

However, due to the rapid elimination of ICG from the circulation, the diagnostic signal strength quickly decreases (Photochem. Photobiol. 2000, 72, 392). Thus, the physician is unable to reliably represent, smaller vessels over a longer period of time. Another disadvantage of ICG are its poor solubility properties. The strong tendency of the ICG molecules to form molecule aggregates on the one hand interferes with the preparation of a complete solution of the substance to be administered. Another disadvantage is the reduced fluorescent activity caused by aggregated ICG molecules (Microvascular Res. 1998, 55; Survey Opthalmol. 2000, 45, 15). Yet another disadvantage of ICG is the instability of the pharmaceutical solution of the active ingredient. The disadvantage of decomposition of the active ingredient in aqueous solvents is also observed in other active ingredients of the class of polymethine dyes. This disadvantageous property prevents the yield of an aqueous solution for injection which entails increased production costs.

The person skilled in the art is aware of several ways for overcoming the disadvantages of the frequently used ICG. First of all, the synthesis of novel fluorescent dyes with improved properties is known in the art. The synthesis of novel fluorescent dyes had led to active ingredients with improved solubility properties and a higher fluorescence quantum yield compared to ICG. However, all known substances have the tendency to leave the vascular system after a certain period of time after injection and to concentrate in the extravascular space (Acad. Radiol. 2006, 13, 4; J Fluoresc. 2005, 15, 443). The process of extravasation starts as early as one minute after intravenous injection. One of the reasons for this behavior is an incomplete bonding to plasma proteins. The extravasation of ICG is prevented by a complete bonding to plasma proteins.

Fluorescence dyes with the tendency to leave the vascular system lead to an increase in the fluorescence signal in the extravascular tissue. This results in a deterioration of the signal-to-background ratio compared to ICG even though the fluorescence quantum yield of the known substances has been improved.

Another method of providing novel fluorescent dyes with improved properties compared to ICG known to the person skilled in the art is the synthesis of dye-protein conjugates (Technol. Cancer Res. Treat. 2004, 3, 393). It is known that coupling to a protein with a molecular weight of more than 70 kDa or generating such molecular weights by conjugating proteins with polyethylene glycols (Adv. Drug Deliv. Rev. 2003, 55, 1261-77), reduces renal elimination to a very high degree. Thus, this results directly in an extended period of circulation. However, this process also leads to new disadvantages compared to ICG. One disadvantage is the increased risk of undesired effects due to the additional use of proteins. It is known that proteins such as albumins or immunoglobulins, which are used as coupling partners, can lead to an increased immune response. Since diagnostic processes require a high degree of drug safety, the use of fluorescent dye-protein conjugates is not preferred. The significantly higher production costs of a fluorescent dye-protein conjugate compared to ICG are another disadvantage.

The preparation of modified pharmaceutical compositions with the goal of obtaining improved properties of ICG is also known. Various pharmaceutical compositions are described in Photochem. Photobiol. 2000, 71, 347 (Rajagopalan et al.), WO2007/025768 (Fischer et al.), Polymeric nanoparticulate delivery system for Indocyanine green: Biodistribution in healthy mice. Int. J. Pharm, 2004, 278, 93-301, Saxena, V. et al.: Enhanced photo-stability, thermal stability and aqueous-stability of indocyanine green in polymeric nanoparticulate systems, J. Photochem. Photobiol. B., 2004, 74, 29-38, WO2004/064751.

It was therefore an object of the present invention to provide nanoparticular formulations with improved properties. These nanoparticular formulations are especially suitable as contrast medium.

The present invention is directed to nanoparticular formulations comprising a PEG-alkyl block copolymer and an NIR (near infrared) fluorescent dye. PEG-alkyl block copolymers are polymeric amphiphilic substances or surface-active agents which in an aqueous medium form defined molecular structures, in particular micelles or emulsions. In the sense of the present invention, micelles are a component of nanoparticular formulations.

Thus, within the framework of the present invention, the term "nanoparticular formulation" refers to essentially separate units comprising the mentioned components. Micelles are an example of such separate units.

Within the framework of the present invention, the term "aqueous medium" refers to an aqueous solution with a water content of at least 75 wt.-%, preferably at least 90 wt.-%. According to the present invention, additional components of the aqueous medium can for example include physiologically compatible components such as salts, for example inorganic salts or organic salts. Inorganic salts include for example chlorides, carbonates, acetates, dihydrogen phosphates, hydrogen phosphates. Organic salts are for example hydrochlorides of TRIS, HEPES, meglumine, lysine, glycine, asparagine. The salts can be combined with acids and bases, for example sodium hydroxide solution, sodium hydrogen carbonate, hydrochloric acid, phosphoric acid, acetic acid, ascorbic acid or citric acid to form buffer systems. Furthermore, such buffer systems can comprise cosolvents, for example ethanol, diethanolamine, glycerine, polyethylene glycol. Other physiologically compatible components include sugars, for example glucose, fructose, saccharose, mannitol, sorbitol, dextran, dextrose. An overview of the buffer systems used in the present invention can be found in Remington's Science and Practice of Pharmacy, 21 ed, Lippincott Williams & Wilkins.

Within the framework of the present invention, PEG-alkyl block copolymers are compounds comprising polyethylene glycol (PEG) or methoxypolyethylene glycol as hydrophilic structural element and an alkyl chain as lipophilic structural element. According to the present invention, polyethylene glycols of 3 to 150 oxyethylene units (—$CH_2CH_2O$—), preferably 3 to 50 oxyethylene units, are preferred. PEGs are not necessarily uniform but rather a mixture consisting of a varying number of oxyethylene units with an average molecular weight. Preferably, the molecular weight of the PEG-alkyl block copolymer is from 200 to 10,000 g/mole. Preferably, the molecular weight of the PEG-alkyl block copolymer is from 250 to 3,000 g/mole. It is especially preferred that the molecular weight of the PEG-alkyl block copolymer be from 300 to 1,000 g/mole. Here, the PEG-alkyl block copolymer is a molecule wherein the hydrophilic and the lipophilic structural element are connected, preferably via a covalent bond.

The average molecular weight of the nanoparticular formulation according to the present invention is preferably in a range of 100,000 to 10,000,000 g/mole. This refers to the average weight of one mole of the separate units formed in the aqueous medium.

The critical micelle concentration (CMC) of the formulation according to the present invention is below 1 wt.-% of PEG-alkyl block copolymer, preferably below 0.1 wt.-%, and especially preferred below 0.01 wt.-% of PEG-alkyl block copolymer. In this connection, the term wt.-% denotes the relative weight percentage in an aqueous formulation.

Within the framework of the present application, the term "alkyl chain" refers to a saturated or unsaturated hydrocarbon chain. The alkyl chain of the present invention is an alkyl chain comprising 3 to 30 carbon atoms which can be independently mono- or poly-substituted with $C_1$-$C_3$ alkyl, hydroxyl or phenyl. Alkyl chains derived from saturated, unsaturated or chemically/biochemically modified fatty acids are preferred. In this connection, chemical or biochemical modifications are in particular selected from the group comprising the following modifications: hydroxylations, epoxidations, acetylations, carboxylations, esterifications, branching with alkyl groups which can optionally comprise one of the above-mentioned modifications.

Saturated fatty acids include for example butyric acid, hexanoic acid, docosanoic acid, tetracosanoic acid, hexacosanoic acid, stearic acid, eicosanoic acid, margaric acid, palmitic acid, myristic acid, lauric acid, decanoic acid, octanoic acid. Unsaturated fatty acids include for example palmitoleic acid, vaccenic acid, elaidic acid, oleic acid, icosenoic acid, nervonic acid, erucic acid, cetoleic acid, linoleic acid, linolenic acid, timnodonic acid, clupanodonic acid, arachidonic acid. Chemically or biochemically modified fatty acids are hydroxy fatty acids or aryl fatty acids, for example 12-hydroxy stearic acid.

Thus, particularly preferred nanoparticular formulations are those wherein the PEG-alkyl block copolymer is a PEG-fatty acid ester block copolymer.

Polyethylene glycol-12-hydroxy stearic acid is particularly preferred.

According to the present invention, fatty acids form a bond to the PEG with the acid group or a derivative of the acid group. Bonds can be ethers, esters, amides, carbamates, thiocarbamates, thioethers, or urea bonds. The terminal hydroxyl group of the PEG can have been converted to an amine, thiol, or another functional group. Direct bonds of the acid group of the fatty acids to the PEG are preferred. Ester bonds are especially preferred.

The invention furthermore relates to PEG-fatty acid ester block copolymers wherein the glycerol as structural element is covalently bonded to the PEG and the fatty acids forms esters with the hydroxyl groups of the glycerol. Polyethylene glycol-polyglycerol-ricinoleate is especially preferred.

NIR-fluorescent dyes are chromophors or fluorophors with near infrared (NIR) fluorescence.

NIR fluorescent dyes which are lipophilic are preferred. Lipophilic NIR fluorescent dyes in the sense of the invention are those carrying at most two functional groups selected from sulfonate, sulfate, carboxyl, polyhydroxyalkyl (4 to 6 hydroxyl groups).

It is especially preferred that the NIR fluorescent dye be selected from the group comprising polymethine dyes, phthalocyanines, naphthalocyanines, triphenylmethines, croconium dyes, squarilium dyes.

It is most preferred that the NIR fluorescent dye be selected from the group comprising polymethine dyes, cyanine dyes, indotricarbocyanines, 3,3'-diethyloxadicarbocyanine iodide (DODCI), 3,3'-diethylthiodicarbocyanine iodide (DTDCI), 3,3'-diethyloxatricarbocyanine iodide (DOTCI), 3,3'-diethylthiotricarbocyanine iodide (DTTCI), indocyanine green.

Preferred indotricarbocyanines are based on benzoindolenines and an unsubstituted or substituted pentamethine chain, as well as an alkyl group substituted with a hydrophilic group at each nitrogen in the benzoindole structure. In particular, the NIR fluorescent dye indocyanine green (ICG, CardioGreen, IC Green, DiagnoGreen) is preferred. In addition to the indocyanine green, derivatives of the indocyanine green are also especially preferred. Derivatives of indocyanine green are the indocyanine green structure with a polymethine chain independently substituted with $C_1$-$C_3$ alkyl, chlorine, $C_1$-$C_3$ alkyloxy and/or an alkyl group which together with the heptamethine chain of the indocyanine green forms a 5- or 6-membered ring.

Derivatives of indocyanine green wherein
a) one or two sulfobutyl chains at the indole nitrogen are substituted with —$C_{1-6}$-alkyl-$R^2$, wherein $R^2$ is selected from the group comprising —OH, —$OSO_3H$, —$OSO_3^-$ $Na^+$, —$NH_2$, —$N_3$, —COOH, —SH, —SO$_3$H, —SO$_3^-$Na$^+$, —C≡C, —C$_{1-20}$-alkyl, —CONH—C$_{1-20}$ alkyl, —NHC(O)—C$_{1-20}$ alkyl and —O—C$_{1-20}$ alkyl, wherein the C$_{1-20}$ alkyl is a branched or straight-chain alkyl in which one or more (preferably one to three) non-consecutive methylene units can be substituted with a unit selected from the group comprising O, S, NH, C(O)NH, SO$_2$, SO, aryl, ethene or ethine, and wherein the alkyl is substituted with at least one (preferably one to three) groups selected from the group comprising —OH, —OSO$_3$H, —OSO$_3^-$Na$^+$, —NH$_2$, —N$_3$, —COOH, —SH, —SO$_3$H, —SO$_3^-$Na$^+$, —C≡C; and/or b) the polymethine chain is substituted with a substituted polymethine chain with a group R$^3$ at the central carbon atom, wherein the two adjacent carbon atoms can form a 5- or 6-membered ring together with the three carbon atoms of the polymethine chain, wherein R$^3$ is selected from the group comprising —C$_{1-6}$-alkyl-R$^2$, -phenyl-C$_{1-6}$alkyl-R$^2$, —S-phenyl-C$_{1-6}$-alkyl-R$^2$, —O-phenyl-C$_{1-6}$alkyl-R$^2$, wherein R$^2$ is as described above, and/or c) the outer benzindole rings are substituted with one or more groups independently selected from —SO$_3^-$Na$^+$, —COOH or —OH are preferred.

Examples of such structures are illustrated in FIG. 8 which shows the structure of ICG and derivatives according to the present invention.

Derivatives of ICG wherein a) two sulfobutyl chains at the indole nitrogen are substituted with —C$_{1-4}$-alkyl-R$^2$, wherein R$^2$ is selected from the group comprising —OH, —OSO$_3$H, —OSO$_3^-$Na$^+$, —COOH, —SO$_3$H, —SO$_3^-$Na$^+$; and/or b) the polymethine chain is substituted with a substituted polymethine chain with a group R$^3$ at the central carbon atom, wherein the two adjacent carbon atoms can form a 6-membered ring together with the three carbon atoms of the polymethine chain, wherein R$^3$ is selected from the group comprising -phenyl-C$_{1-6}$alkyl-R$^2$, —O-phenyl-C$_{1-6}$alkyl-R$^2$, wherein R$^2$ represents —COOH or —SO$_3^-$Na$^+$, and/or c) the outer benzindole rings are substituted with one or two —SO$_3^-$Na$^+$ each are especially preferred.

A schematic view of the derivatives of the indocyanine green (FIG. 8A) is shown in FIG. 8B.

The diameter of the nanoparticular formulation according to the present invention can be in a range of 1 nm to 1,000 nm, preferably 5 nm to 500 nm, especially preferred 5 nm to 50 nm.

The fluorescence or NIR fluorescence of the formulations according to the present invention is in a range of 600 nm to 1,000 nm, preferably 750 nm to 900 nm.

The fluorescence quantum yield of the formulations according to the present invention is at least as high as a dye solution in water, however, preferably twice as high, and especially preferred four times as high. For indocyanine green, the fluorescence quantum yield in the nanoparticular formulation is at least 4%, especially preferred at least 8%.

Compared with a purely aqueous formulation, quenching, i.e. a decrease in the fluorescence intensity when the concentration is increased, only occurs at higher concentrations in the case of the formulations according to the present invention. Preferably, quenching does not occur until a concentration of more than 0.1 mg/mL is reached. In the case of indocyanine green, quenching preferably occurs at a concentration 10 times higher than a purely aqueous solution.

Moreover, formulations according to the present invention can be provided in higher concentrations than purely aqueous formulations of the dyes. A concentration of at least 0.5 mg/mL is preferred, preferably at least 1 mg/mL.

The storage stability of the formulations according to the present invention is significantly improved compared with purely aqueous formulations and the formulations described in Saxena et al. Seven days after production more than 90% of the formulated NIR fluorescent dye can still be detected in intact form.

The plasma protein binding of the ICG in the formulations according to the present invention corresponds to that of ICG. After incubation of a micelle formulation in human serum and measurement of the free portion of ICG after an incubation period of 4 h and removal of the unbound ICG by means of ultra centrifugation, a free portion of <5% is determined. This value is obtained in the analogous experiment with an aqueous solution of ICG.

Compared to an aqueous solution of ICG (absorption maximum 780 nm), the absorption maximum of ICG in the micelle formulation von ICG of 797 nm is shifted to higher wavelengths by 17 nm (red shift). Due to the optical properties of tissue, this shift leads to an increased penetration depth of the excitation light and thus an improved detection in tissues. Furthermore, the absorption maximum at 797 nm is close to the absorption maximum of ICG in blood plasma (805 nm). Established diagnostic devices are adjusted to this wavelength so that this property allows a direct use of the formulation.

The present invention furthermore relates to a pharmaceutical composition comprising a nanoparticular formulation according to the present invention.

The present invention also relates to a nanoparticular formulation according to the present invention for use as contrast medium.

Another object of the present invention is a process for the preparation of a nanoparticular formulation comprising the following steps:

The essential steps of the preparation of a nanoparticular formulation are (1) dissolving the PEG-alkyl block copolymer in water, preferably obtaining a concentration of 0.05 to 1 g/mL (2) adding the fluorescent dye to the solution to form a micellic formulation.

DESCRIPTION OF THE DRAWINGS

FIG. 4C: Stability of ICG (0.005% ICG) in Brij® 58 micelles.

The invention is described in more detail in the following examples:

EXAMPLES

Example 1

Preparation of the Micelle Formulation

Example 1: 2 g Solutol HS 15 are heated to 65° C. 10 ml water for injection purposes are added under stirring and the clear solution is cooled to room temperature. 50 mg ICG are dissolved in the micelle solution and sterilized by filtration through a 0.2 µm membrane filter.

Example 2: 2 g Solutol HS 15 are added to 10 ml water for injection purposes under stirring at room temperature. A clear solution is obtained. 50 mg ICG are dissolved in the micelle solution and sterilized by filtration through a 0.2 µm membrane filter.

Absorption and Fluorescence Measurements

Absorption spectra in a wavelength range of 700 nm to 900 nm were recorded with a UVIKON 933 Spectrophotometer (company Kontron) in the various solvents.

→ICG in water λmax=780 nm

Figure 1A:
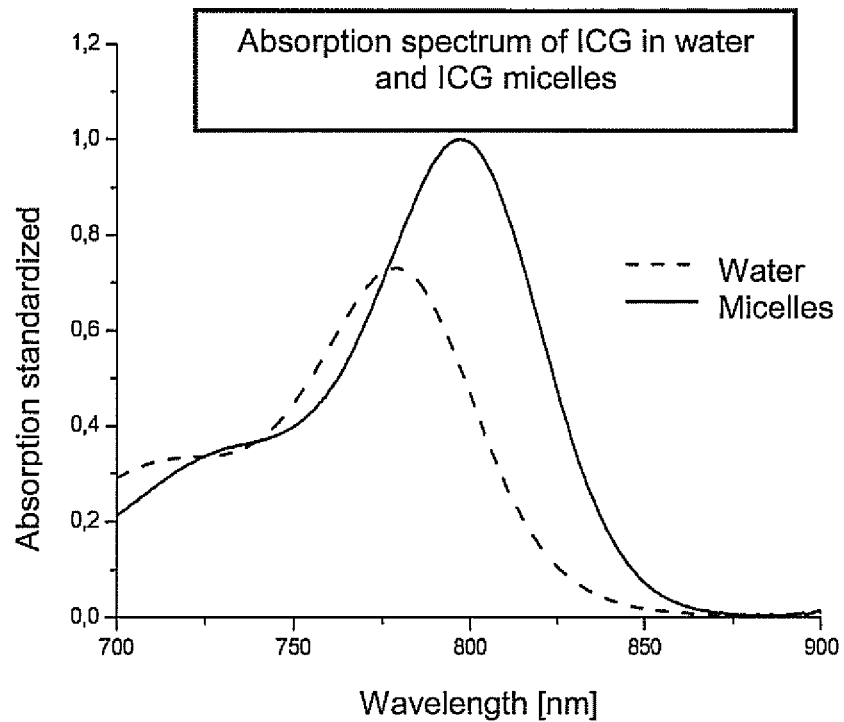
FIG. 1A: Absorption spectrum of ICG in water (dotted line) and ICG micelles in water after preparation according to Example 1 (solid line). Standardization to micelle solution=1.

ICO micelles λmax=797 nm (FIG. 1A)

Fluorescence measurements were carried out by means of a FluoroLog-2 Spectrofluorometer (350 W Xenon lamp) of the company Spex. For this purpose, emission spectra of 700 nm to 900 nm were recorded. The excitation wavelength corresponded to the respective maximum of the formulation in the absorption spectrum (ICG in water λmax=780 nm and ICG micelles λmax=795 nm). Due to the s & r modus of the software DM 3000, the different lamp intensities of the different excitation wavelengths could be taken into account in the evaluation.

The quantum yield is calculated via the surface area below the emission curve. ICG in DMSO was used as the standard ($\Phi$=0.13).

Figure 1B:
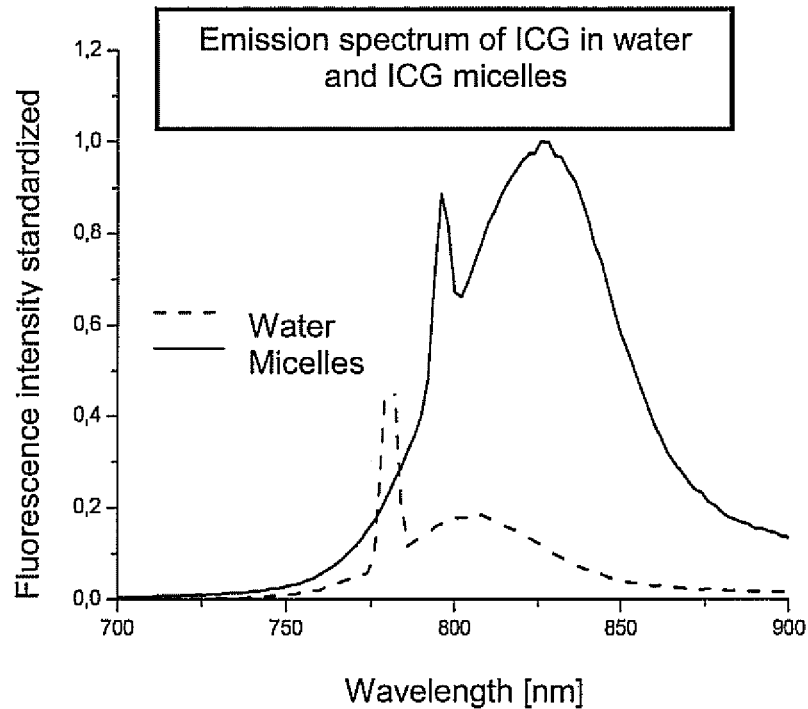
FIG. 1B: Fluorescence emission spectrum of ICG in water (dotted line) and ICG micelles in water after preparation according to Example 1 (solid line). Standardization to micelle solution=1.
Figure 1C:
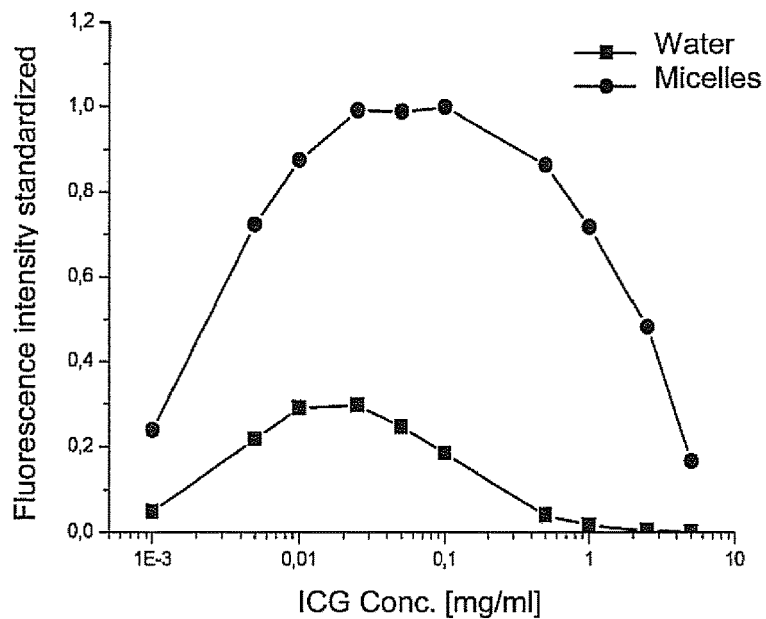
FIG. 1C: Fluorescence intensity of ICG in water (squares) and of the ICG micelles in water as a function of the concentration of ICG (0.001 mg/mL to 5 mg/mL).

→ The quantum yield of ICG micelles is $\Phi$=0.08 compared to ICG in water $\Phi$=0.02. Quenching only takes place at higher concentrations (starting at 0.1 mg/ml ICG) (FIG. 1B and FIG. 1C).

Stability Tests

Figure 1D:
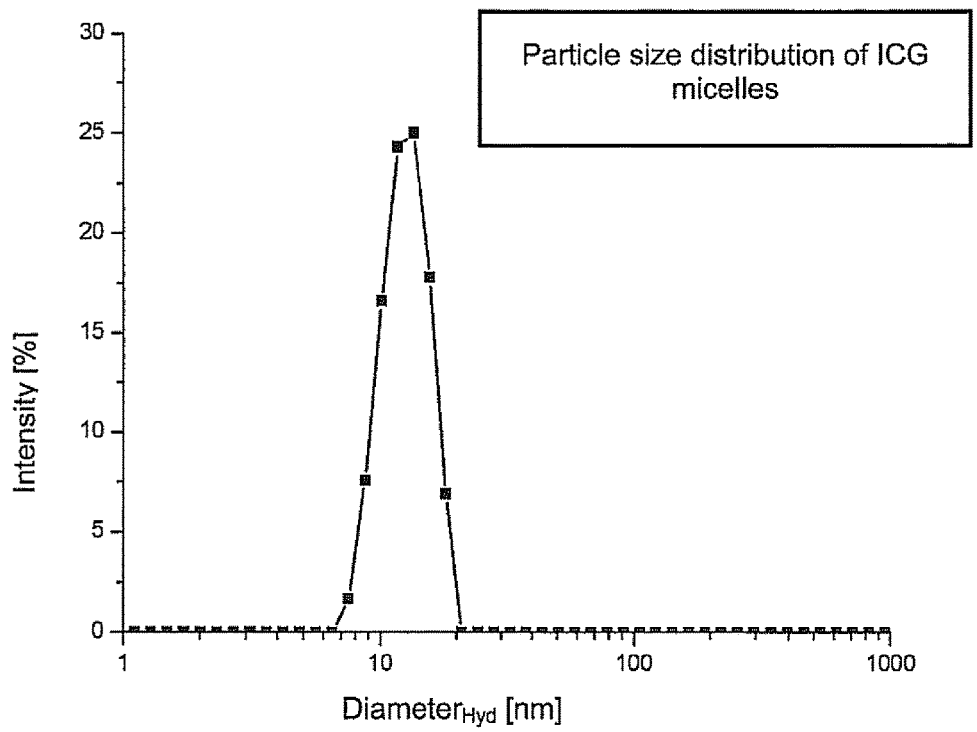
FIG. 1D: Particle size distribution by means of dynamic light-scattering.
Figure 1E:
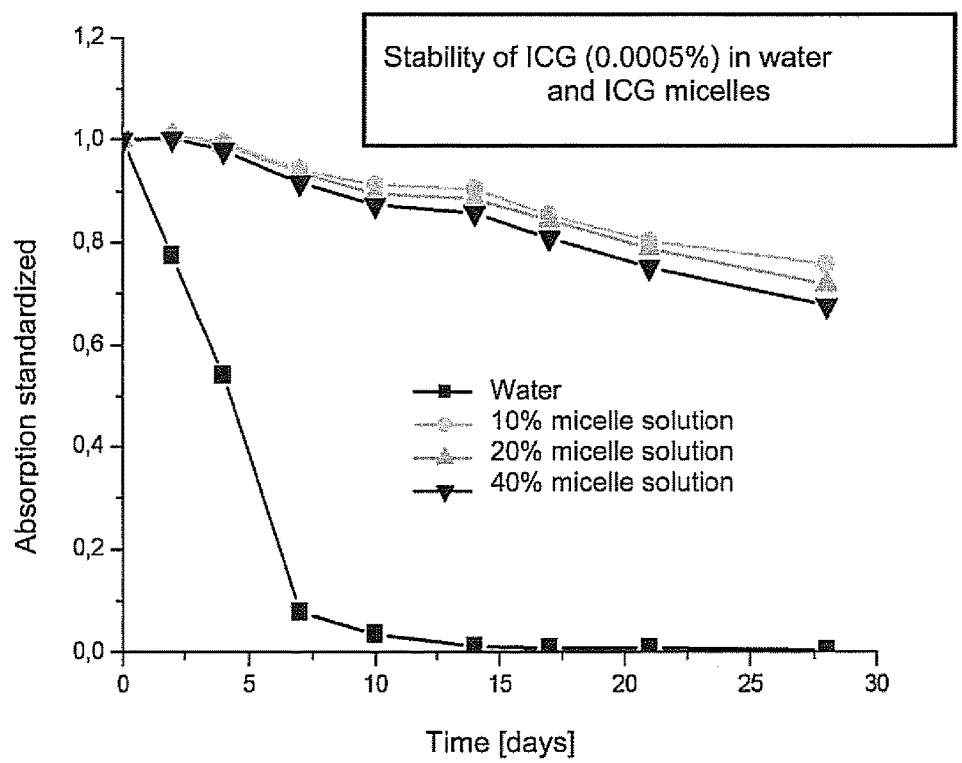
FIG. 1E: Determination of stability by measuring the absorption in the maximum of the various formulations as a function of time. Comparison of ICG in water (squares) and three ICG micelle formulations; Solutol 10% (circles), 20% (triangles), 40% (inverted triangles).

For the stability test the absorption in the maximum of the various formulations was measured as a function of time. For this purpose, 0.0005% ICG solutions were prepared and stored at room temperature. The storage of the purely aqueous ICG formulation shows a reduction of the standardized absorption to below 10% after only 7 days. The micelle formulations of ICG on the other hand still show more than 90% of the absorption after 7 days of storage compared to the initial value, and even after 4 weeks, absorption does not fall below 70% (FIG. 1E).

Particle Size

The particle size distribution was determined by means of dynamic light-scattering (Zetasizer NS, company Malvern). Measurement was carried out with a He—Ne-Laser (633 nm, 4 mW) from an angle of 173°. The samples were measured directly without dilution in 45 µl quartz cuvettes.

→ ICG micelles have a hydrodynamic diameter of 12 nm at a PDI (polydispersity index) of 0.061. (FIG. 1D)

Plasma Protein Binding

The wavelength shift in the absorption spectrum was observed to determine the plasma protein binding. For this purpose, spectra of 700 nm to 900 nm of ICG in water and in plasma were compared with spectra of ICG micelles in water and in plasma.

→ In both formulations, the absorption maximum in plasma shifts to 805 nm. The behavior of the plasma protein binding of the ICG in the formulations of the present invention corresponds to that of ICG in an aqueous medium.

Hemolysis Assay

For the examination of the hemolytic activity of ICG micelles, heparinized human whole blood was first removed from the plasma and washed 3 times with PBS buffer. After the preparation of a 2% erythrocyte suspension in PBS, it was incubated with the ICG micelle formulation for 1 h at 37° C. Pure PBS solution was used as blank reading value (0% hemolysis) and 2% triton solution was used as 100% hemolysis value. After incubation, the erythrocytes were centrifuged off and the red pigmentation in the supernatant was determined photometrically at 540 nm.

→ ICG micelles show no hemolytic activity.

PEG-Alkyl Compounds

Example 2

0.3 g Cithrol 10 MS (PEG 20 stearat) are dissolved in 10 ml water for injection purposes under stirring at room temperature. A clear solution is obtained. 50 µl of a 1% (w/v) 50 mg ICG solution are dissolved in the micelle solution and sterilized by filtration through a 0.2 µm membrane filter.

Absorption and Fluorescence Measurements

Absorption spectra were recorded in a wavelength range of 600 nm to 900 nm with a DU®530 Beckman Spectralphotometer in the various solvents.

→ICG in water λmax=779 nm

Figure 2A:
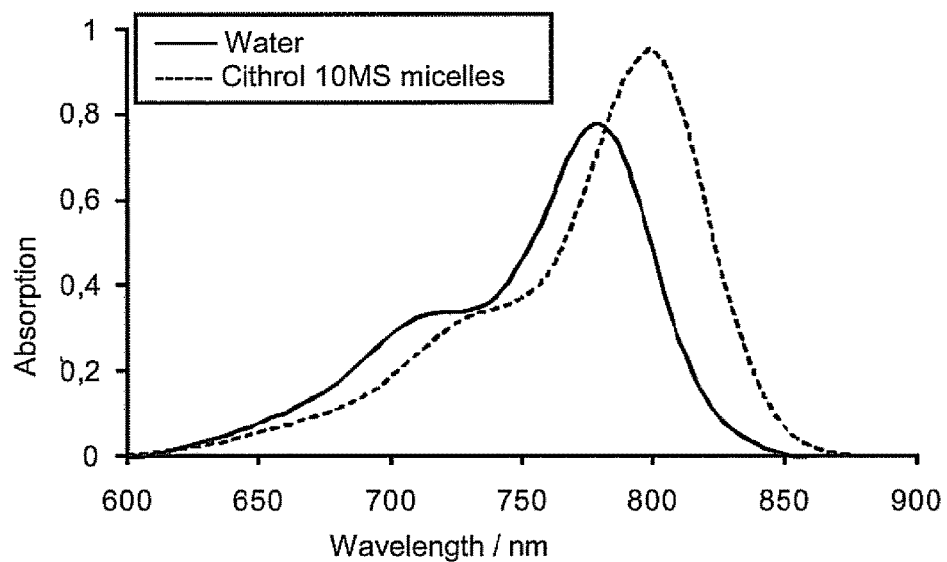
FIG. 2A: Absorption spectra of ICG in water and ICG Cithrol 10MS micelles.

ICG-Cithrol 10 MS micelles λmax=800 nm (FIG. 2A)

Fluorescence measurements were carried out by means of a Spectrofluorometer FP-6500 of the company JASCO. For this purpose, emission spectra of 770 to 900 nm were recorded. The excitation wavelength was 760 nm in each case. The quantum yield is calculated via the surface area below the emission curve. ICG in DMSO was used as the standard ($\Phi$=0.12).

Figure 2B:
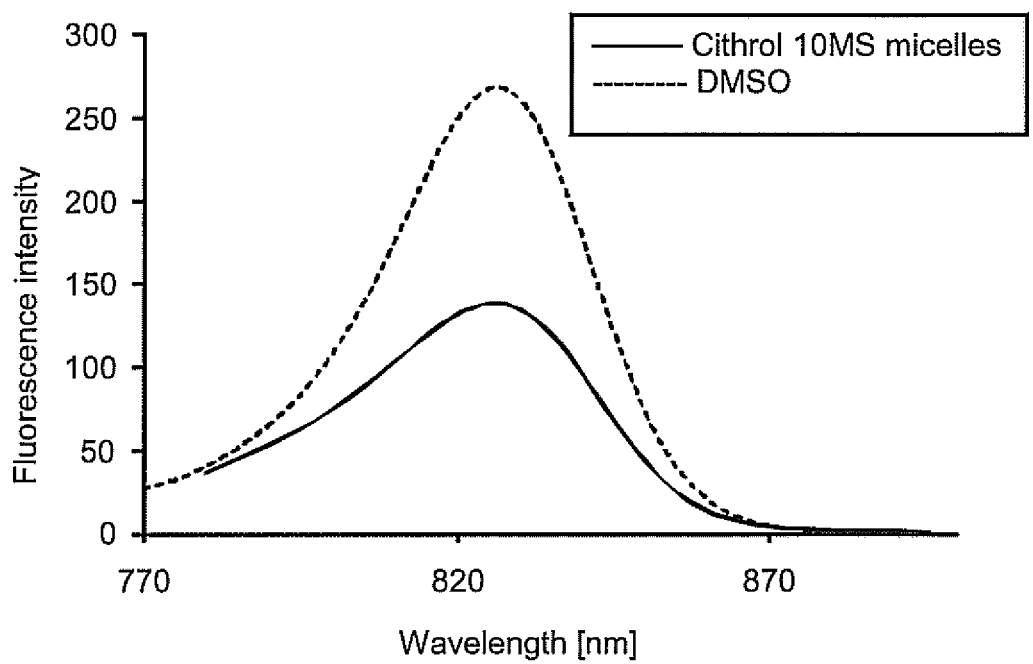
FIG. 2B: Emission spectrum of ICG in DMSO and Cithrol 10MS micelles.

The quantum yield of ICG-Cithrol 10 MS micelles is $\phi$=0.08 compared to ICG in water at $\phi$=0.02 (FIG. 2B).

Stability Tests

Figure 2C:
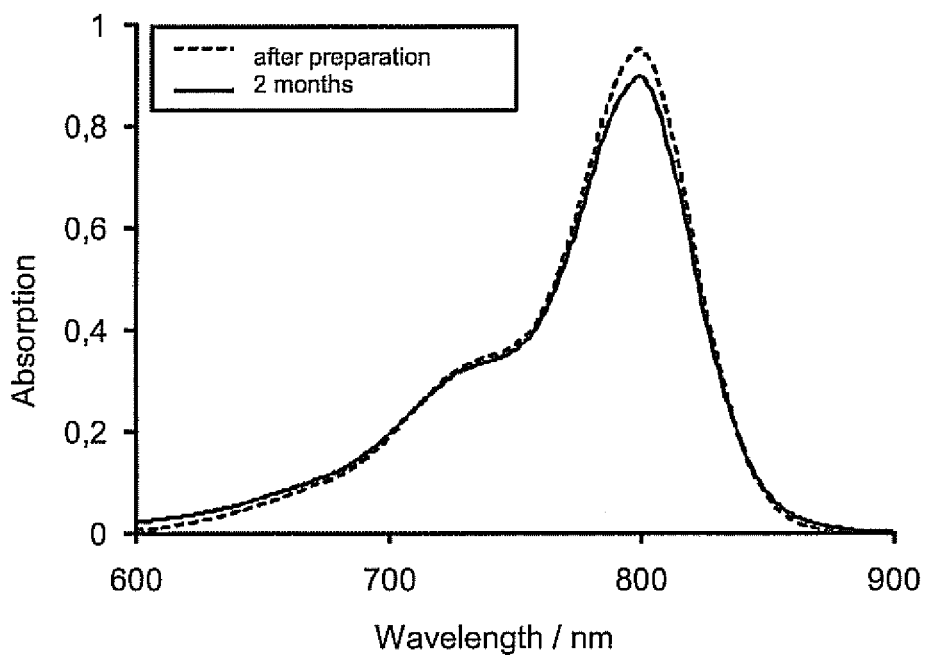
FIG. 2C: Stability of ICG (0.005% ICG) in Cithrol 10MS micelles.

For the stability test the absorption spectra of the various formulations were measured as a function of time. After 2 months of storage at 4° C. and under exclusion of light, the Cithrol 10MS micelle formulations of ICG still showed more than 94% of absorption compared to the initial value (FIG. 2C).

Example 3

0.4 g Crodet S40 LD (PEG 40 Stearat) are dissolved in 10 ml water under stirring at room temperature for injection purposes. A clear solution is obtained. 50 µl of a 1% (w/v) ICG solution are dissolved in the micelle solution and sterilized by filtration through a 0.2 µm membrane filter.

Absorption and Fluorescence Measurements

Absorption spectra were recorded in a wavelength range of 600 nm to 900 nm with a DU®530 Beckman Spectralphotometer in the various solvents.

→ICG in water λmax=779 nm

Figure 3A:
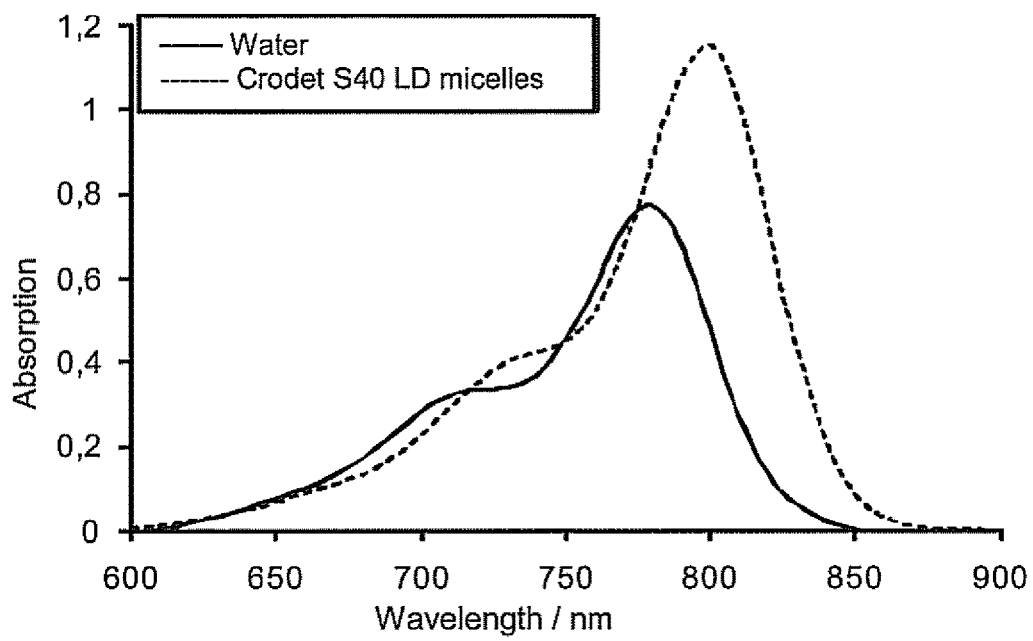
FIG. 3A: Absorption spectra of ICG in water and ICG-Crodet S40 LD micelles.

ICG-Crodet S40 LD micelles λmax=800 nm (FIG. 3A)

Fluorescence measurements were carried out by means of a Spectrofluorometer FP-6500 of the company JASCO. For this purpose, emission spectra of 770 to 900 nm were recorded. The excitation wavelength was 760 nm in each case. The quantum yield is calculated via the surface area below the emission curve. ICG in DMSO was used as the standard ($\Phi$=0.12).

Figure 3B:
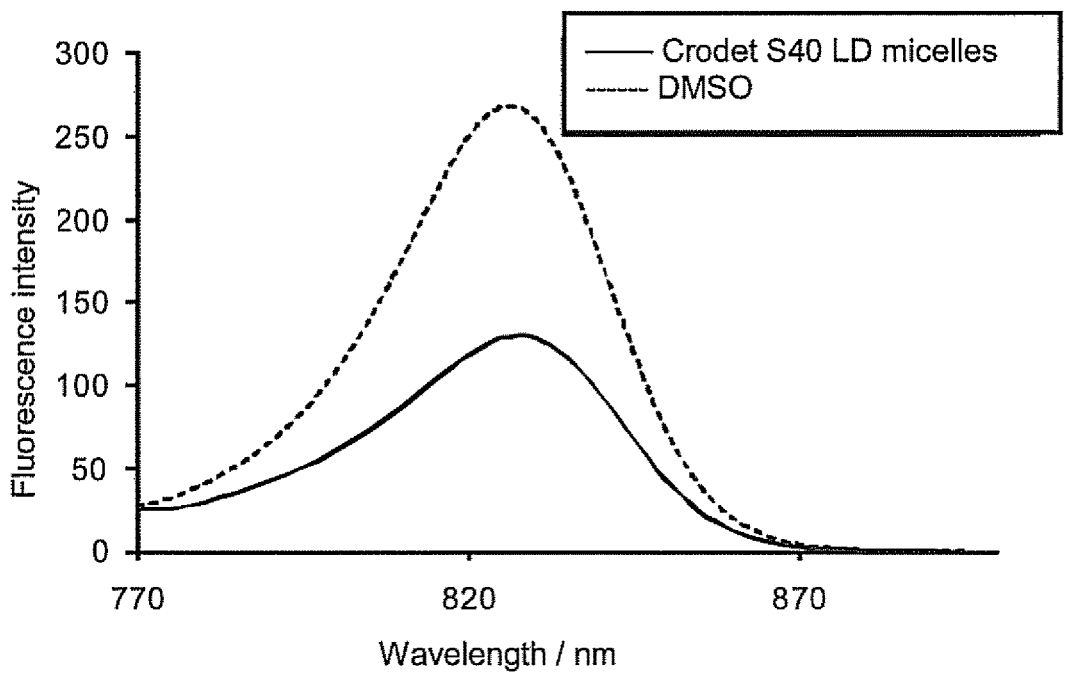
FIG. 3B: Emission spectrum of ICG in DMSO and Crodet S40 LD micelles.

→ The quantum yield of ICG-Crodet S40 LD micelles is $\phi$=0.07 compared to ICG in water at $\phi$=0.02 (FIG. 3B).

Stability Tests

Figure 3C:
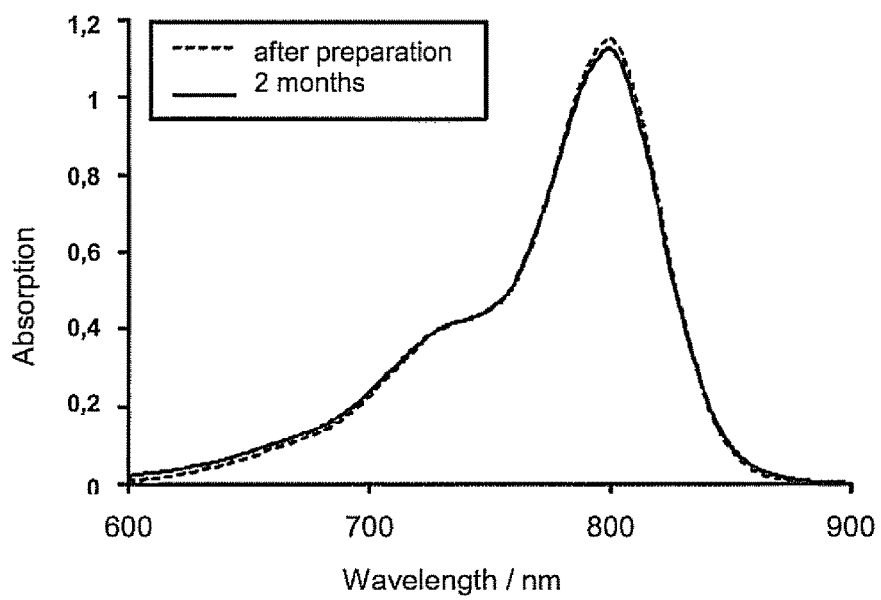
FIG. 3C: Stability of ICG (0.005% ICG) in Crodet S 40 micelles.

For the stability test the absorption spectra of the various formulations were measured as a function of time. After 2 months of storage at 4° C. and under exclusion of light, the Crodet S40 LD micelle formulations of ICG still showed more than 97% of absorption compared to the initial value (FIG. 3C).

Example 4

0.5 g Brij® 58 (PEG 20 cetylether) are dissolved in 10 ml water for injection purposes under stirring at room temperature. A clear solution is obtained. 50 µl of a 1% (w/v) 50 mg ICG solution are dissolved in the micelle solution and sterilized by filtration through a 0.2 µm membrane filter.

Absorption and Fluorescence Measurements

Absorption spectra were recorded in a wavelength range of 600 nm to 900 nm with a DU®530 Beckman Spectralphotometer in the various solvents.

ICG in water λmax=779 nm

Figure 4A:
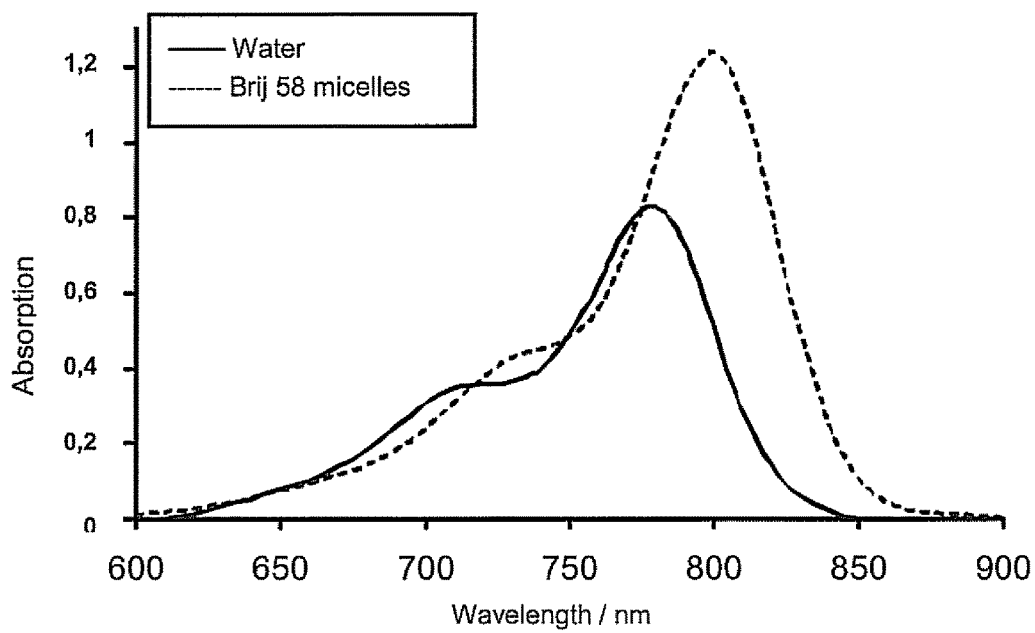
FIG. 4A: Absorption spectra of ICG in water and ICG-Brij® 58 micelles.

ICG-Brij® 58 micelles λmax=800 nm (FIG. 4A)

Fluorescence measurements were carried out by means of a Spectrofluorometer FP-6500 of the company JASCO. For this purpose, emission spectra of 770 to 900 nm were recorded. The excitation wavelength was 760 nm in each case. The quantum yield is calculated via the surface area below the emission curve. ICG in DMSO was used as the standard=0.12).

Figure 4B:
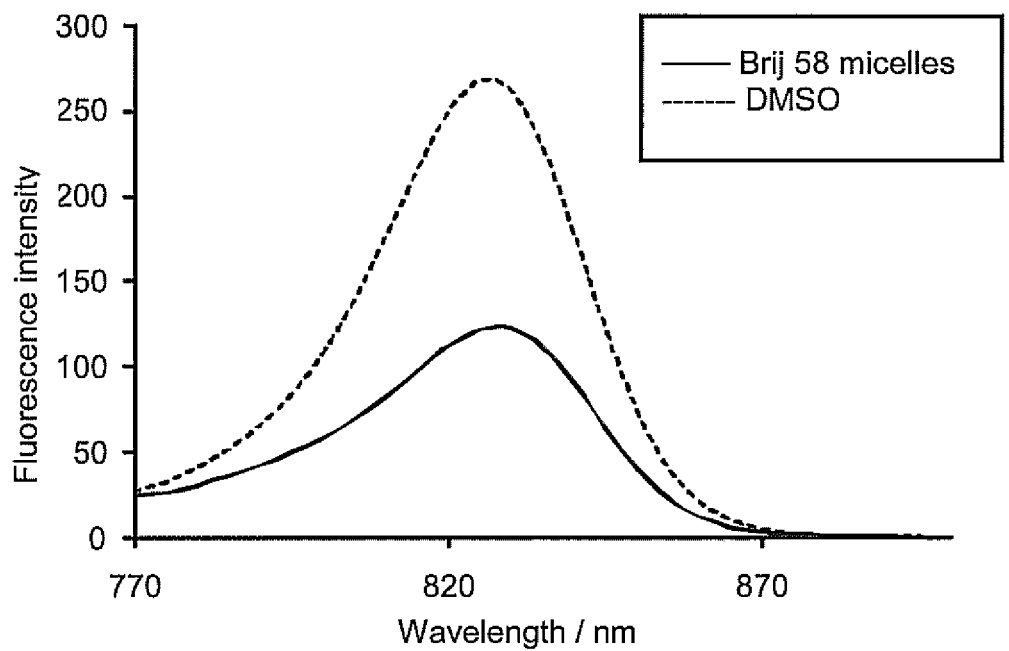
FIG. 4B: Emission spectrum of ICG in DMSO and Brij® 58 micelles.
Figure 4B:
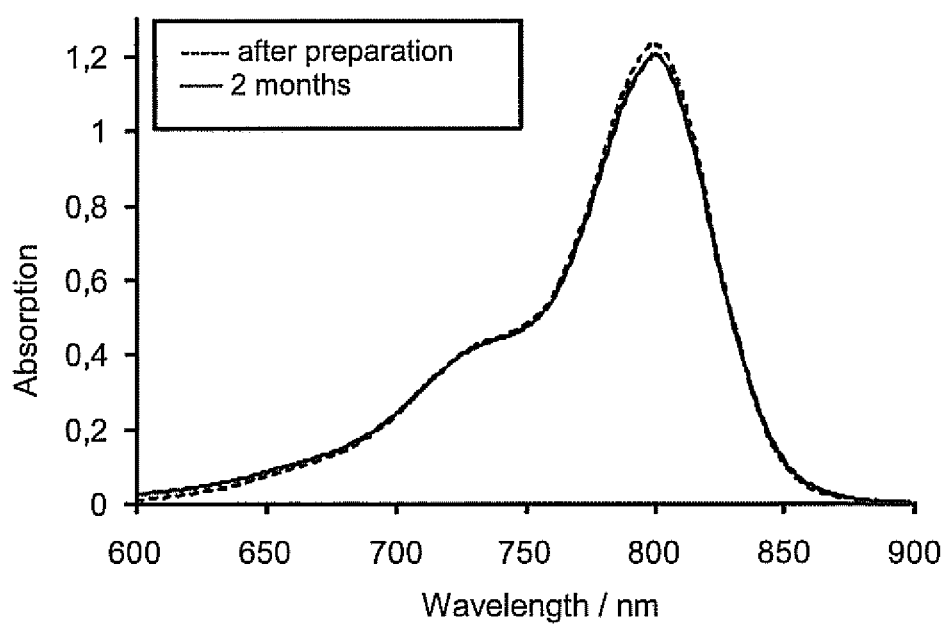

→ The quantum yield of ICG-Brij® 58 LD micelles is $\phi$=0.06 compared to ICG in water at $\phi$=0.02 (FIG. 4B).

Stability Tests

For the stability test the absorption spectra of the various formulations were measured as a function of time. After 2 months of storage at 4° C. and under exclusion of light, the Brij® 58 micelle formulations of ICG still showed more than 97% of absorption compared to the initial value.

Example 5

1 g Brij® 98 (PEG 20 oleylether) are dissolved in 10 ml for injection purposes water under stirring at room temperature. A clear solution is obtained. 50 µl of a 1% (w/v) ICG solution are dissolved in the micelle solution and sterilized by filtration through a 0.2 µm membrane filter.

Absorption and Fluorescence Measurements

Absorption spectra were recorded in a wavelength range of 600 nm to 900 nm with a DU®530 Beckman Spectralphotometer in the various solvents.

ICG in water λmax=779 nm

Figure 5A:
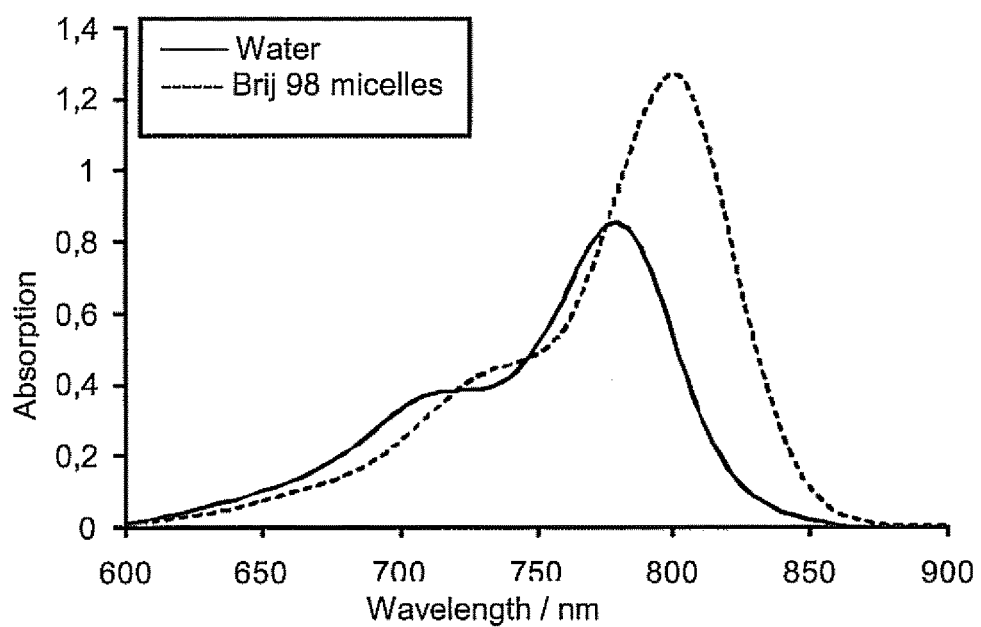
FIG. 5A: Absorption spectra of ICG in water and ICG-Brij® 98 micelles.

ICG-Brij® 98 micelles λmax=800 nm (FIG. 5A)

Fluorescence measurements were carried out by means of a Spectrofluorometer FP-6500 of the company JASCO. For this purpose, emission spectra of 770 to 900 nm were recorded. The excitation wavelength was 760 nm in each case. The quantum yield is calculated via the surface area below the emission curve. ICG in DMSO was used as the standard ($\Phi$=0.12).

Figure 5B:
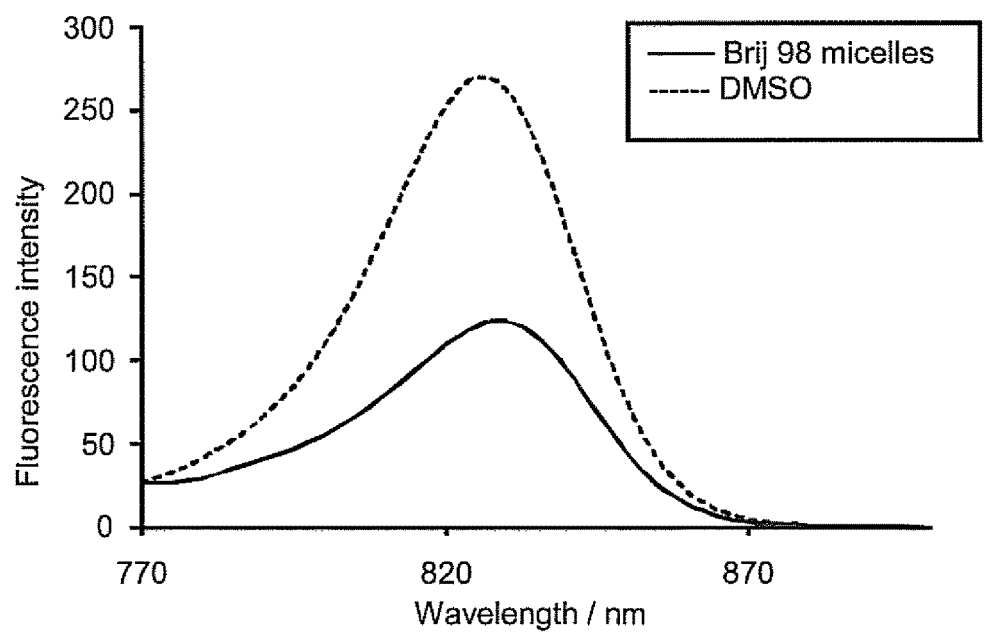
FIG. 5B: Emission spectrum of ICG in DMSO and Brij® 98 micelles.

→ The quantum yield of ICG-Brij® 98 LD micelles is $\phi$=0.06 compared to ICG in water at $\phi$=0.02 (FIG. 5B).

Stability Tests

Figure 5C:
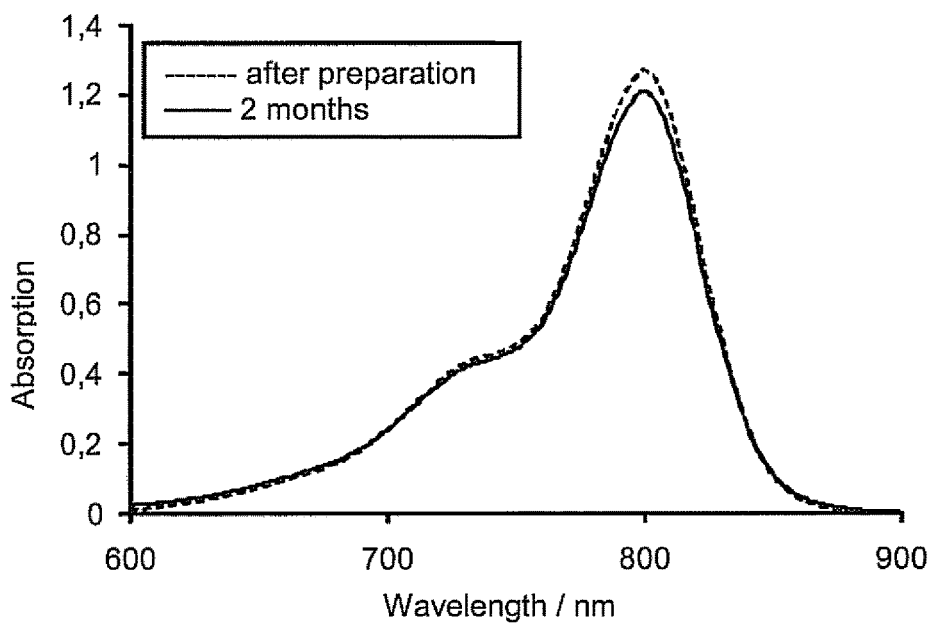
FIG. 5C: Stability of ICG (0.005% ICG) in Brij® 98 micelles.

For the stability test the absorption spectra of the various formulations were measured as a function of time. After 2 months of storage at 4° C. and under exclusion of light, the Brij® 98 micelle formulations of ICG still showed more than 95% of absorption compared to the initial value (FIG. 5C).

ICG-Derivatives

Example 6

Figure 6A:
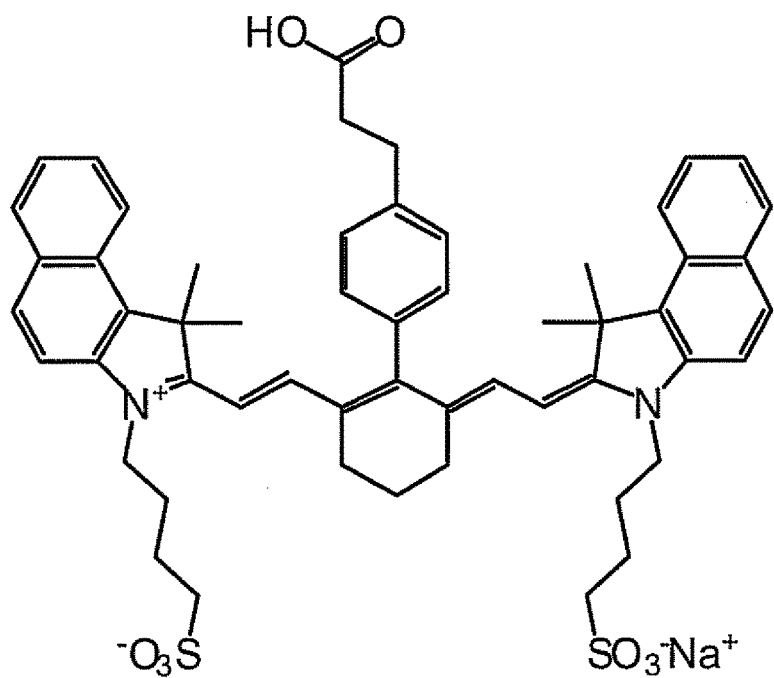
FIG. 6A: Structure of the ICG derivative NW003.5.

1 g Solutol® HS 15 is dissolved in 10 ml water for injection purposes under stirring at room temperature. A clear solution is obtained. 50 µl of a 1% (w/v) NW003.5 solution (FIG. 6A) are dissolved in the micelle solution and sterilized by filtration through a 0.2 µm membrane filter.

Absorption and Fluorescence Measurements

Absorption spectra were recorded in a wavelength range of 600 nm to 900 nm with a DU®530 Beckman Spectralphotometer in the various solvents.

→NW003.5 in water λmax (monomer)=788 nm

Figure 6B:
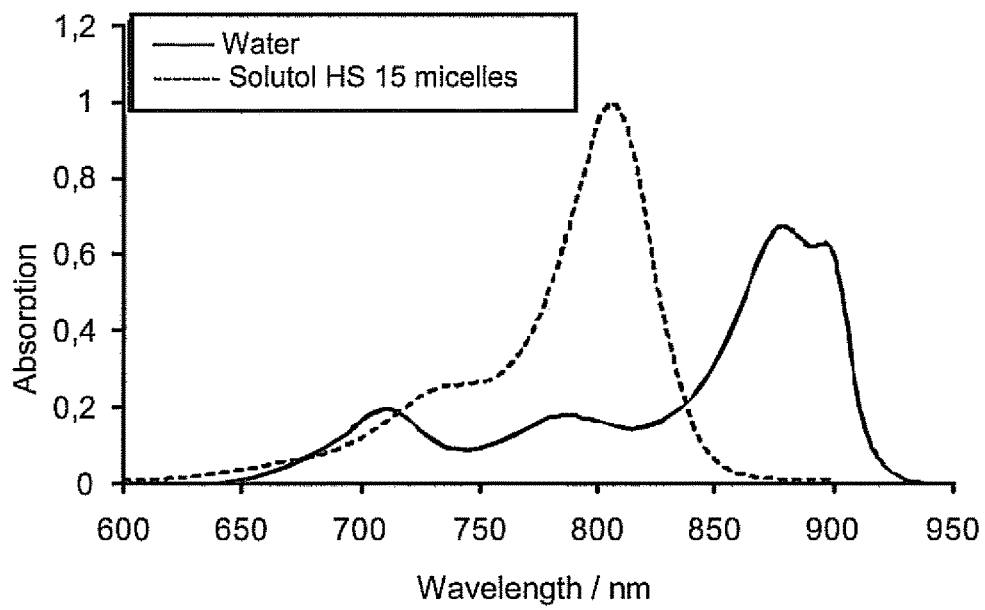
FIG. 6B: Absorption spectra of NW003.5 in water and NW003.5-Solutol HS 15 micelles.

NW003.5-Solutol® HS 15 micelles λmax=806 nm (FIG. 6B)

Figure 6C:
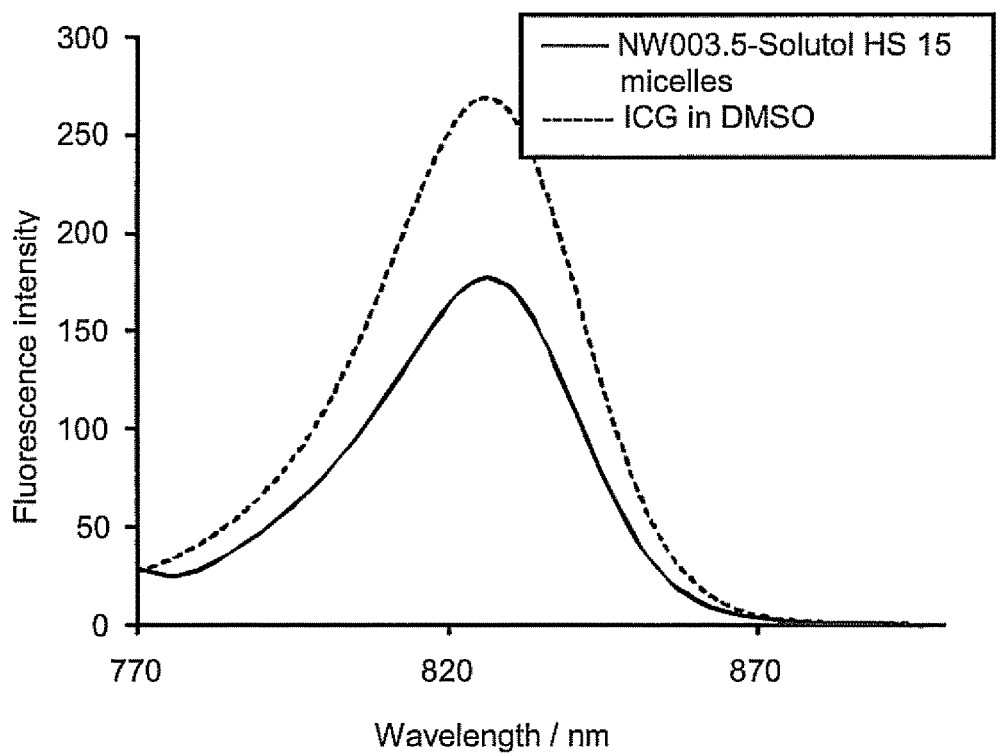
FIG. 6C: Emission spectrum of ICG in DMSO and NW003.5-Solutol HS 15 micelles.
Figure 6D:
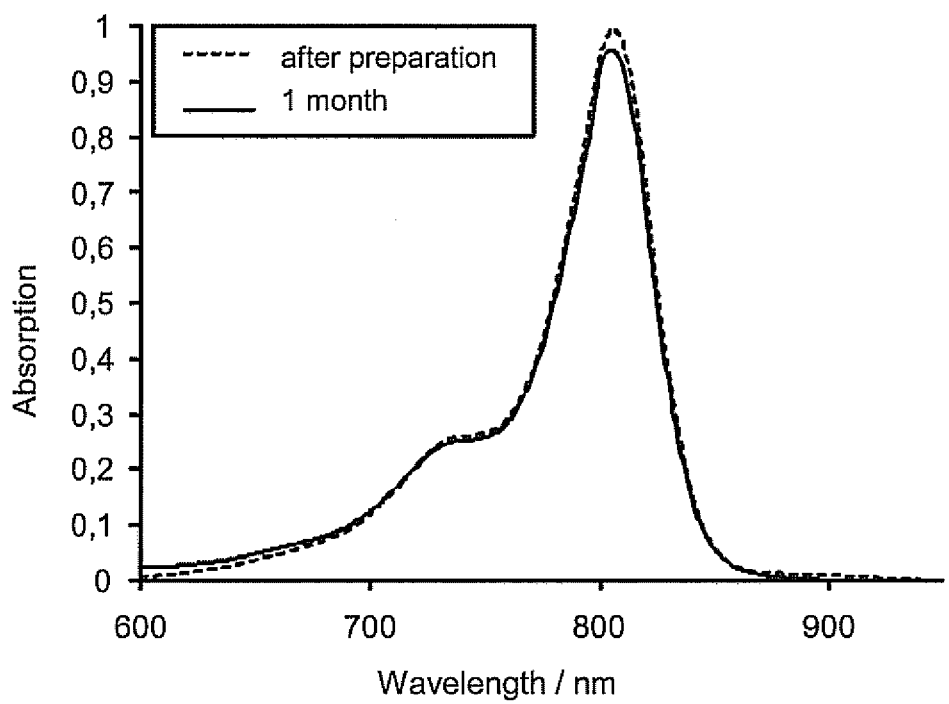
FIG. 6D: Stability of NW003.5 (0.005% NW003.5) in Solutol HS 15 micelles.

The fluorescence measurements were carried out by means of a Spectrofluorometer FP-6500 of the company JASCO. For this purpose, emission spectra of 770 to 900 nm were recorded. The excitation wavelength was 760 nm in each case. The quantum yield is calculated via the surface area below the emission curve. ICG in DMSO was used as the standard ($\Phi$=0.12).
→ The quantum yield of NW003.5-Solutol® HS 15 micelles is $\phi$=0.12 compared to ICG in water at $\phi$=0.02 (FIG. 6C).

Stability Tests

For the stability test the absorption spectra of the various formulations were measured as a function of time. After 1 month of storage at 4° C. and under exclusion of light, the Solutol HS 15 micelle formulations of NW003.5 still showed more than 95% of absorption compared to the initial value.

Example 7

Figure 7A:
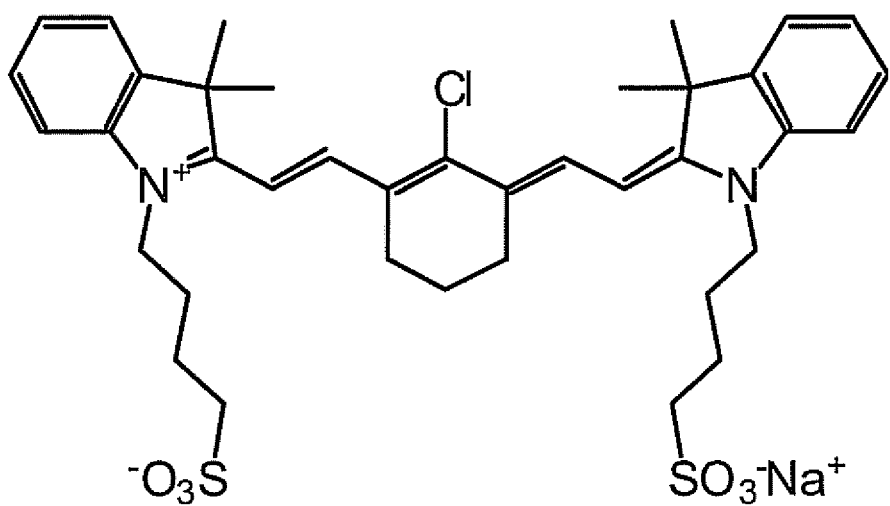
FIG. 7A: Structure of the ICG derivative IR-783.

1 g Solutol® HS 15 is dissolved in 10 ml water for injection purposes. Under stirring at room temperature A clear solution is obtained. 50 µl of a 1% (w/v) IR-783 solution (FIG. 7A) are dissolved in the micelle solution and sterilized by filtration through a 0.2 µm membrane filter.

Absorption and Fluorescence Measurements

Absorption spectra were recorded in a wavelength range of 600 nm to 900 nm with a DU®530 Beckman Spectra'photometer in the various solvents.

→IR-783 in water λmax (Monomer)=775 nm

Figure 7B:
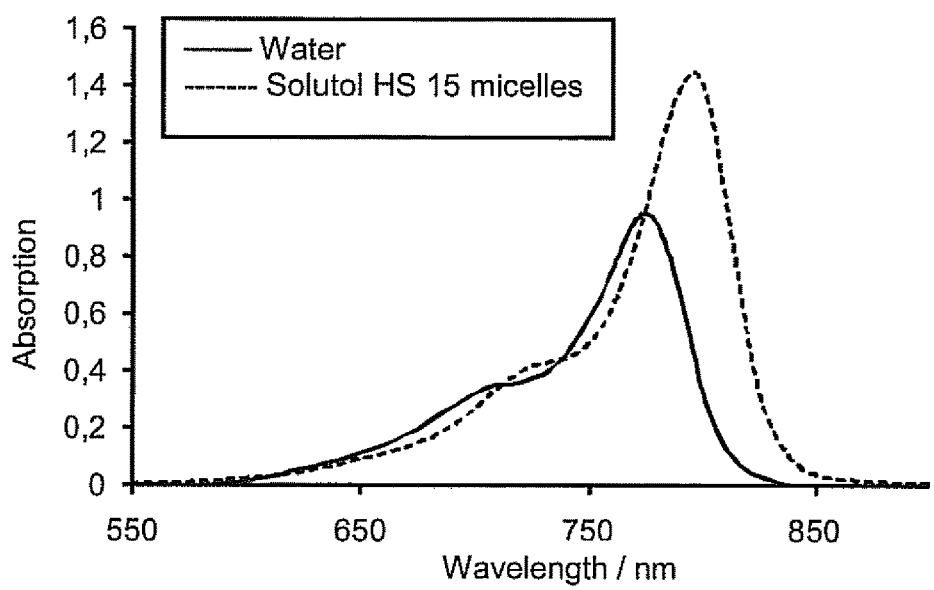
FIG. 7B: Absorption spectra of IR-783 in water and IR-783-Solutol HS 15 micelles.

IR-783-Solutol® HS 15 micelles λmax=797 nm   (FIG. 7B)

Figure 7C:
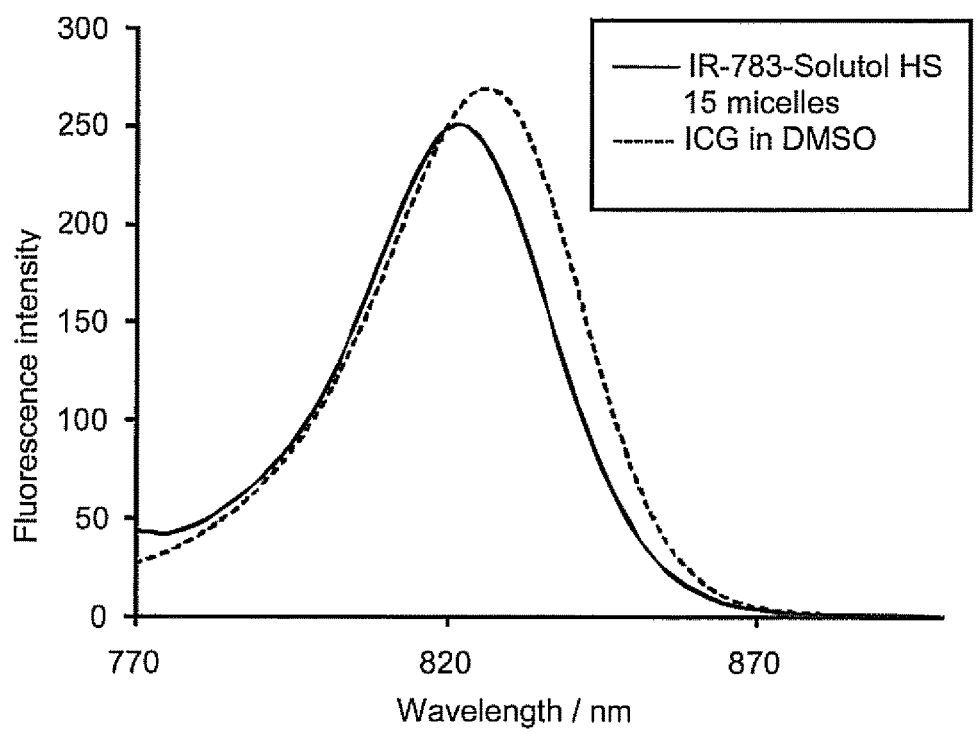
FIG. 7C: Emission spectrum of ICG in DMSO and IR-783-Solutol HS 15 micelles.
Figure 7D:
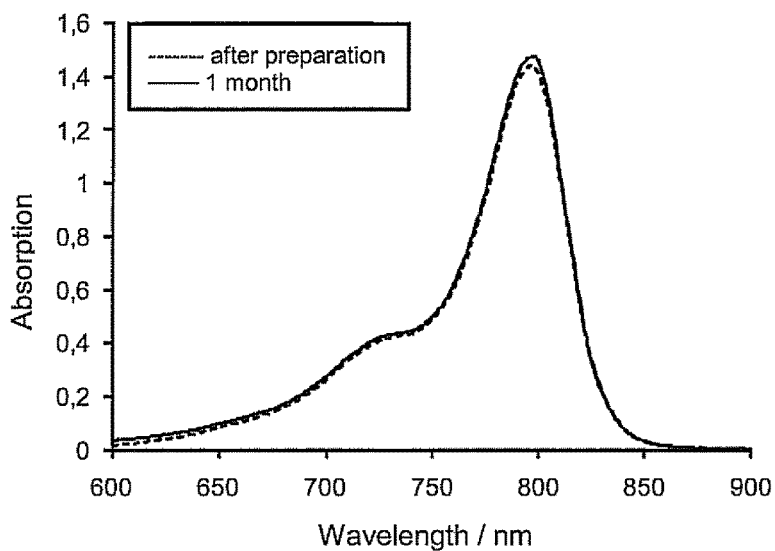
FIG. 7D: Stability of IR-783 (0.005% IR-783) in Solutol HS 15 micelles.
Figure 8A:
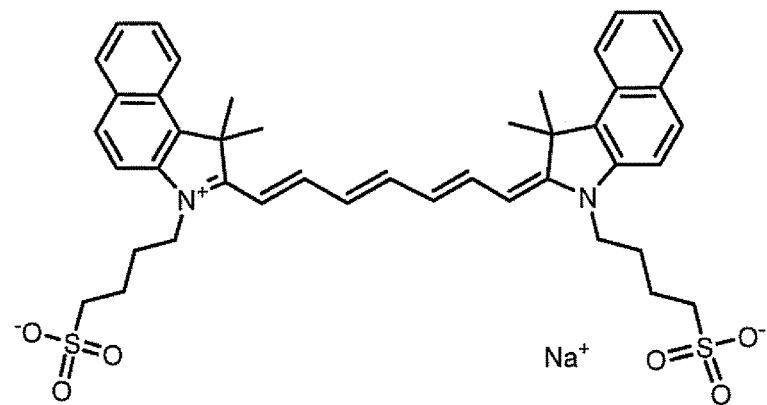
FIG. 8: Schematic view of exemplary dyes for use in the present invention; a) indocyanine green (ICG); b) derivatives of the indocyanine green for use in the present invention.
Figure 8B:
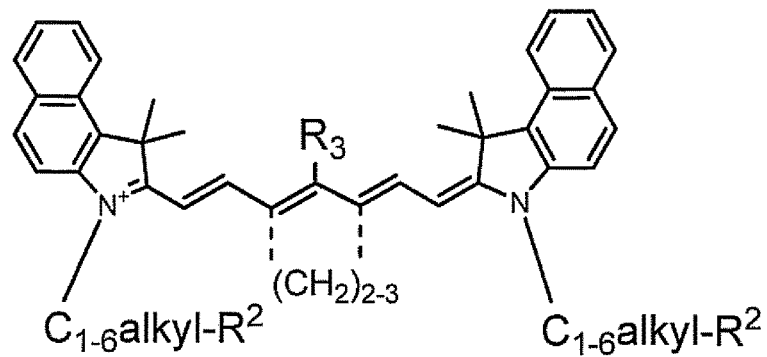

Fluorescence measurements were carried out by means of a Spectrofluorometer FP-6500 of the company JASCO. For this purpose, emission spectra of 770 to 900 nm were recorded. The excitation wavelength was 760 nm in each case. The quantum yield is calculated via the surface area below the emission curve. ICG in DMSO was used as the standard ($\Phi$=0.12).
→ The quantum yield of IR-783-Solutol® HS 15 micelles is $\phi$=0.11 compared to ICG in water at $\phi$=0.02 (FIG. 7C).

Stability Tests

For the stability test the absorption spectra of the various formulations were measured as a function of time. After 1 month of storage at 4° C. and under exclusion of light, the Solutol HS 15 micelle formulations of IR-783 showed no significant change in absorption compared to the initial value.

The invention claimed is:

1. A micellic formulation, comprising
1) a compound (1) comprising polyethylene glycol or methoxypolyethylene glycol as hydrophilic structural element and an alkyl chain as lipophilic structural element, wherein the alkyl chain has 3 to 30 carbon atoms, which are optionally independently mono- or poly-substituted with $C_1$-$C_3$ alkyl, hydroxyl or phenyl, and wherein the hydrophilic and the lipophilic structural elements are connected via a covalent bond, which covalent bond is an ether, ester, amid, carbamate, thiocarbamate, thioether, or urea bond,
and
2) a near infrared fluorescent dye (2), which is indocyanine green or a derivative of indocyanine green, in which derivative of indocyanine green
   a) one or two sulfobutyl chains at the indole nitrogen are substituted with —$C_{1-6}$-alkyl-$R^2$, wherein $R^2$ is selected from the group consisting of —OH, —$OSO_3H$, —$OSO_3^-$$Na^+$, —$NH_2$, —$N_3$, —COOH, —SH, —$SO_3H$, —$SO_3^-Na^+$, —C≡C, —$C_{1-20}$-alkyl, —CONH—$C_{1-20}$ alkyl, —NHC(O)—$C_{1-20}$ alkyl and —O—$C_{1-20}$ alkyl, wherein the $C_{1-20}$ alkyl is a branched or straight-chain alkyl in which one or more non-consecutive methylene units can be substituted with a unit selected from the group consisting of O, S, NH, C(O)NH, $SO_2$, SO, aryl, ethene and ethine, and wherein the alkyl is substituted with at least one group selected from the group consisting of —OH, —$OSO_3H$, —$OSO_3^-Na^+$, —$NH_2$, —$N_3$, —COOH, —SH, —$SO_3H$, —$SO_3^-Na^+$, and —C≡C; and/or
   b) the polymethine chain is substituted with a substituted polymethine chain with a group $R^3$ at the central carbon atom, wherein the two adjacent carbon atoms can form a 5- or 6-membered ring together with the three carbon atoms of the polymethine chain, wherein $R^3$ is selected from the group consisting of —$C_{1-6}$-alkyl-$R^2$, -phenyl-$C_{1-6}$alkyl-$R^2$, —S-phenyl-$C_{1-6}$alkyl-$R^2$, —O-phenyl-$C_{1-6}$alkyl-$R^2$, and —O-phenyl-$C_{1-6}$alkyl-$R^2$, wherein $R^2$ is defined as above; and/or
   c) the outer benzindole rings are substituted with one or more groups independently selected from the group consisting of —$SO_3^-Na^+$, —COOH and —OH,
      wherein micelles have been formed in an aqueous media from the combination consisting of only the compound (1) and the near infrared fluorescent dye (2),
      wherein the diameter of the micelles is in a range of 1 nm to 50 nm, and
      wherein the fluorescence of the micelles is in a range of 750 to 900 nm.

2. The micellic formulation according to claim 1, wherein the alkyl chain is derived from a saturated, unsaturated or chemically or biochemically modified fatty acid.

3. The micellic formulation according to claim 1, wherein the near infrared fluorescent dye is a derivative of indocyanine green, in which derivative of indocyanine green
   a) one or two sulfobutyl chains at the indole nitrogen are substituted with —$C_{1-6}$-alkyl-$R^2$, wherein $R^2$ is selected from the group consisting of —OH, —$OSO_3H$, —$OSO_3^-Na^+$, —$NH_2$, —$N_3$, —COOH, —SH, —$SO_3H$, —$SO_3^-Na^+$, —C≡C, —$C_{1-20}$-alkyl, —CONH—$C_{1-20}$ alkyl, —NHC(O)—$C_{1-20}$ alkyl and —O—$C_{1-20}$ alkyl, wherein the $C_{1-20}$ alkyl is a branched or straight-chain alkyl in which one or more non-consecutive methylene units can be substituted with a unit selected from the group consisting of O, S, NH, C(O)NH, $SO_2$, SO, aryl, ethene and ethine, and wherein the alkyl is substituted with at least one group selected from the group consisting of —OH, —$OSO_3H$, —$OSO_3^-Na^+$, —$NH_2$, —$N_3$, —COOH, —SH, —$SO_3H$, —$SO_3^-Na^+$, and —C≡C; and/or
   b) the polymethine chain is substituted with a substituted polymethine chain with a group $R^3$ at the central carbon atom, wherein the two adjacent carbon atoms can form a 5- or 6-membered ring together with the three carbon atoms of the polymethine chain, wherein $R^3$ is selected from the group consisting of —$C_{1-6}$-alkyl-$R^2$, -phenyl-$C_{1-6}$alkyl-$R^2$, —S-phenyl-$C_{1-6}$alkyl-$R^2$, —O-phenyl-$C_{1-6}$alkyl-$R^2$, and —O-phenyl-$C_{1-6}$alkyl-$R^2$, wherein $R^2$ is defined as above; and/or
   c) the outer benzindole rings are substituted with one or more groups independently selected from the group consisting of —$SO_3^-Na^+$, —COOH and —OH.

4. The micellic formulation according to claim 1, wherein the near infrared fluorescent dye is indocyanine green.

5. A pharmaceutical composition comprising the micellic formulation according to claim 1 and a pharmaceutically acceptable carrier.

6. A contrast medium suitable for in vivo administration, comprising the micellic formulation according to claim 1, which formulation is in a form suitable for in vivo administration.

7. A process for preparing the micellic formulation according to claim 1, comprising dissolving the compound comprising polyethylene glycol or methoxypolyethylene glycol as hydrophilic structural element and an alkyl chain as lipophilic structural element in water, and adding the fluorescent dye to the solution, wherein a micellic formulation is formed.

8. The micellic formulation according to claim 1, wherein the alkyl chain has been hydroxylated, epoxidated, acetylated, carboxylated or esterified.

9. The micellic formulation according to claim 1, wherein the alkyl chain is a hydroxy stearic acid.

10. The micellic formulation according to claim 1, wherein the polyethylene glycol is a polyethylene glycol fatty acid ester block copolymer.

11. The micellic formulation according to claim 1, wherein the covalent bond is an ether, ester, amid, carbamate, thiocarbamate, or thioether bond.

12. The micellic formulation according to claim 1, wherein the hydrophilic structural element is polyethylene glycol.

13. The micellic formulation according to claim 1, wherein the hydrophilic structural element is methoxypolyethylene glycol.

14. The micellic formulation according to claim 1, which has a hydrodynamic diameter of 12 nm.

15. The micellic formulation according to claim 1, wherein the hydrophilic and the lipophilic structural elements are connected via a covalent bond and form a polyethylene glycol-alkyl block copolymer having a molecular weight of 250 to 3,000 g/mole.

16. The micellic formulation according to claim 15, wherein the polyethylene glycol-alkyl block copolymer has a molecular weight of 300 to 1,000 g/mole.

17. The micellic formulation according to claim 1, which has a fluorescence of 797 nm.

18. The micellic formulation according to claim 1, wherein the compound (1) is present in the aqueous media at a 1 weight % concentration.

19. A micellic formulation, comprising
1) a compound (1) comprising polyethylene glycol or methoxypolyethylene glycol as hydrophilic structural element and an alkyl chain as lipophilic structural element, wherein the alkyl chain has 3 to 30 carbon atoms, which are optionally independently mono- or poly-substituted with $C_1$-$C_3$ alkyl, hydroxyl or phenyl, and wherein the hydrophilic and the lipophilic structural elements are connected via a covalent bond, which covalent bond is an ether, ester, amid, carbamate, thiocarbamate, thioether, or urea bond, and
2) a near infrared fluorescent dye (2), which is indocyanine green or a derivative of indocyanine green, in which derivative of indocyanine green a) one or two sulfobutyl chains at the indole nitrogen are substituted with —$C_{1-6}$-alkyl-$R^2$, wherein $R^2$ is selected from the group consisting of —OH, —$OSO_3H$, —$OSO_3^-Na^+$—$NH_3$—$N_3$, —COOH, —SH, —$SO_3H$, —$SO_3^-Na^+$, —C≡C, —$C_{1-20}$-alkyl, —CONH—$C_{1-20}$ alkyl, —NHC(O)—$C_{1-20}$ alkyl and —O—$C_{1-20}$ alkyl, wherein the $C_{1-20}$ alkyl is a branched or straight-chain alkyl in which one or more non-consecutive methylene units can be substituted with a unit selected from the group consisting of O, S, NH, C(O)NH, $SO_2$, SO, aryl, ethene and ethine, and wherein the alkyl is substituted with at least one group selected from the group consisting of —OH, —$OSO_3H$, —$OSO_3^-Na^+$, —$NH_2$, —$N_3$, —COOH, —SH, —$SO_3H$, —$SO_3^-Na^+$, and —C≡C; and/or b) the polymethine chain is substituted with a substituted polymethine chain with a group $R^3$ at the central carbon atom, wherein the two adjacent carbon atoms can form a 5- or 6-membered ring together with the three carbon atoms of the polymethine chain, wherein $R^3$ is selected from the group consisting of —$C_{1-6}$-alkyl-$R^2$, -phenyl-$C_{1-6}$alkyl-$R^2$, —S-phenyl-$C_{1-6}$alkyl-$R^2$, —O-phenyl-$C_{1-6}$alkyl-$R^2$, and —O-phenyl-$C_{1-6}$alkyl-$R^2$, wherein $R^2$ is defined as above; and/or c) the outer benzindole rings are substituted with one or more groups independently selected from the group consisting of —$SO_3^-Na^+$, —COOH and —OH, wherein micelles have been formed in an aqueous media from the combination consisting of only the compound (1) and the near infrared fluorescent dye (2), wherein the diameter of the micelles is in a range of 1 nm to 50 nm, wherein the fluorescence of the micelles is in a range of 750 to 900 nm, and wherein the micellic formulation contains micelles having a structure wherein the dye (2) is encapsulated by the compound (1).

20. The micellic formulation according to claim 1, which has a 4 times higher fluorescence quantum yield compared to the near infrared fluorescent dye (2) in water.

21. The micellic formulation according claim 1, which has a 4 times higher fluorescence quantum yield compared to the near infrared fluorescent dye (2) in water, wherein the infrared fluorescent dye (2) is indocyanine green.

* * * * *